United States Patent [19]

Ohtsuka et al.

[11] 4,007,279
[45] Feb. 8, 1977

[54] FUNGICIDES

[75] Inventors: Takaaki Ohtsuka; Keigo Satake; Shiro Yamazaki; Takeo Watanabe, all of Iwaki, Japan

[73] Assignee: Kureha Kagaku Kogyo Kabushiki Kaisha, Tokyo, Japan

[22] Filed: Jan. 28, 1975

[21] Appl. No.: 544,895

[30] Foreign Application Priority Data

Jan. 31, 1974 Japan .............................. 49-12257
Sept. 11, 1974 Japan ............................ 49-103864

[52] U.S. Cl. .............................. 424/277; 260/327 P
[51] Int. Cl.$^2$ ...................................... C07D 339/08
[58] Field of Search ................. 260/327 P; 424/277

[56] References Cited
UNITED STATES PATENTS 2,991,292  7/1961  Degener et al. .................... 260/327

OTHER PUBLICATIONS

Van Schoor et al., Ger. Pat. No. 1060655 (cited as C.A. 55:7748).

Primary Examiner—Henry R. Jiles
Assistant Examiner—C. M. S. Jaisle
Attorney, Agent, or Firm—Holman & Stern

[57] ABSTRACT

A fungicidal compound having a general structure corresponding to a member selected from the group of 2,3-dicyano-5,6-dihydro-p-dithiin and its 5-alkyl derivatives, as expressed by the following general formula:

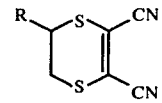

wherein R stands for H or an alkyl radical of $C_1 - C_6$.

8 Claims, 8 Drawing Figures

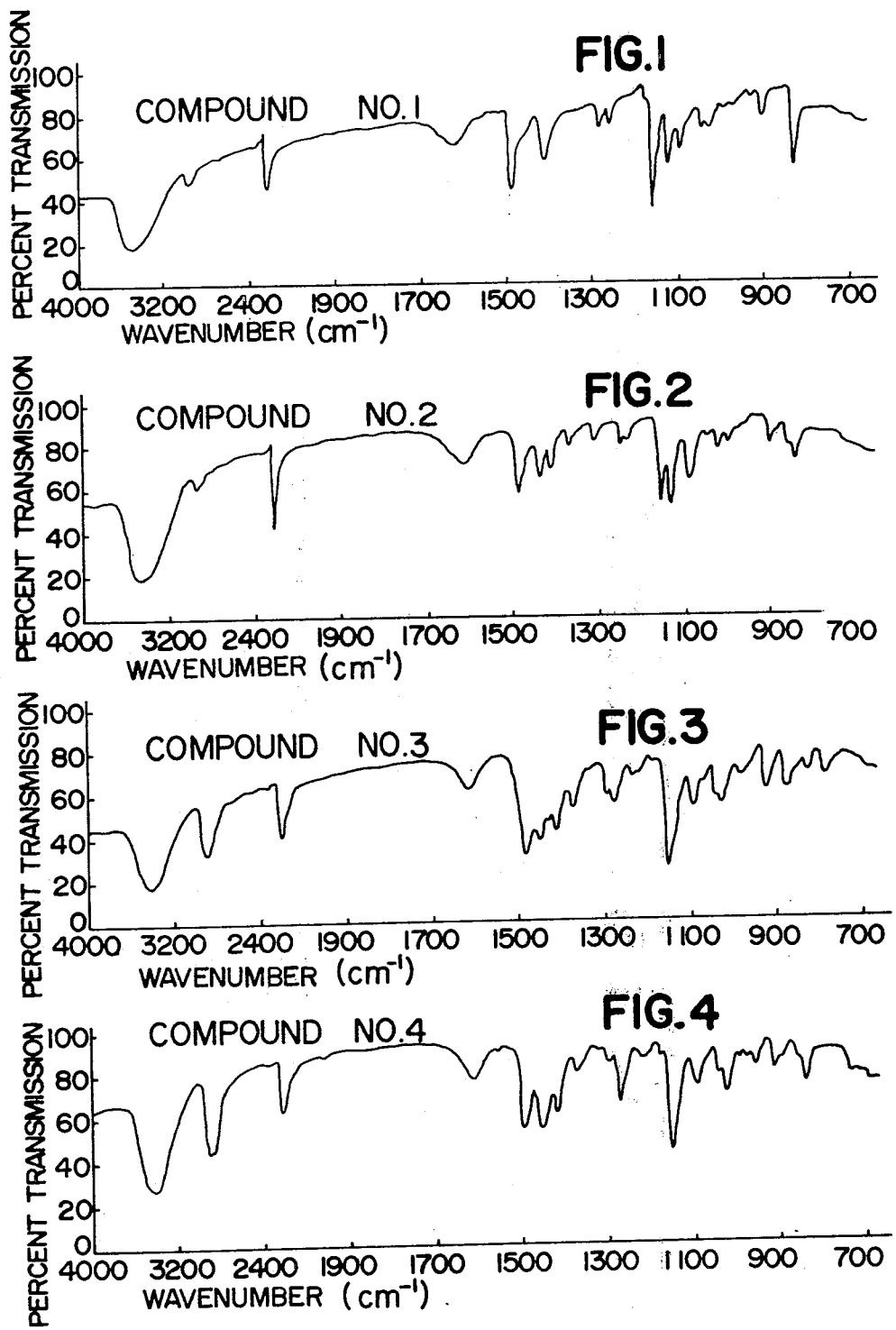

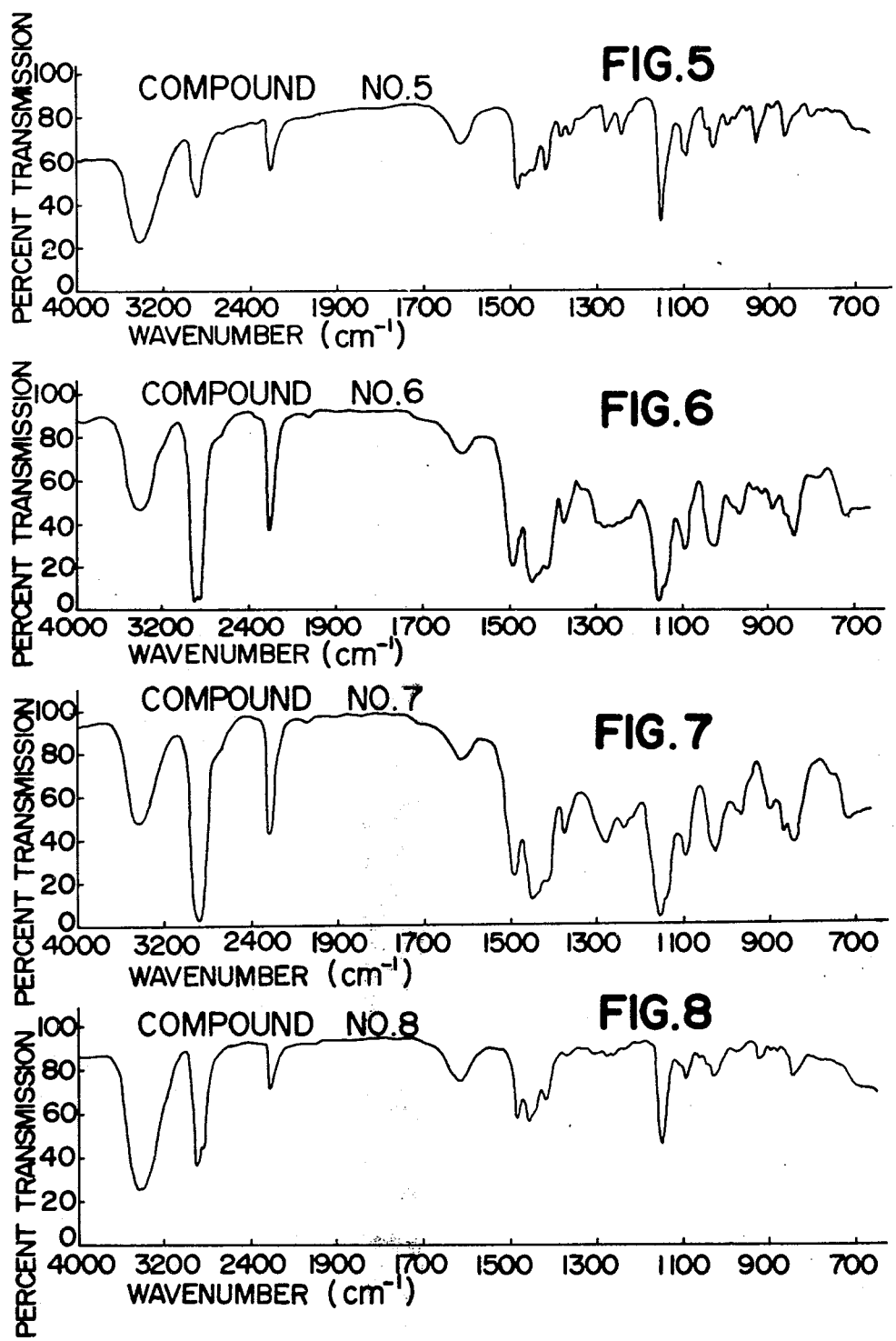

FUNGICIDES

BACKGROUND OF THE INVENTION

1. Field of the Invention

This invention relates to novel compounds adapted for use in the control of plant diseases.

The invention further relates to a fungicidal composition for use in the same purpose as above, and including as its effective substance at least one of said compounds, as will be later more fully described.

2. Object of the Invention

The main purpose of the present invention is to provide the above kind of compounds and compositions which rapidly decompose upon being applied onto the plant, thus representing no appreciable residual characteristic remaining per se in the earth and thus no apparent adverse and poisonous effects upon human bodies.

SUMMARY OF THE INVENTION

This invention resides in fungicidal compounds and compositions adapted for the control of plant diseases, said compositions having, as their effective substance, at least a member selected from the group consisting of 2,3-dicyano-5,6-dihydro-p-dithiin as expressed by the following general formula:

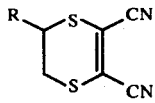

wherein R stands for H or an alkyl of $C_1 - C_6$, and its 5-alkyl derivatives.

The aforementioned compesitions are highly effective for the control of various plant diseases, for example, powdery and downy mildews of leaf- and fruit vegetables; and rice blast. They are specifically and superiorly effective for the control of plant mildew diseases, recently raising the problem of strong and irreparable immunoreactions to substantial known fungicides.

As will be later more fully described, the aforementioned chemical compounds are highly safe to living plants. As an example, they do remarkably not represent any harmful effect, even in the highest possible atmospheric temperature in summer seasons, as high as 40° C, upon living plants, thus being astonishingly superior as the active agent for the above purposes, especially for the fungicidal control of house-cultured plants.

According to our experimental results, the aforementioned compounds have a strong tendency of early decomposition upon once applied to affected living plants, thus giving no rise to extended residence on plants and in soil. Therefore, the practical use of these compounds does not provide any fear of harmful effect upon manipulating personels by a residual amount of the fungicide, or of polution of the related environment.

The above compounds are novel, with exception of 2,3-dicyano-5,6-dihydro-p-dithiin and 2,3-dicyano-5,6-dihydro-5-methyl-dithiin.

In order to prepare the above compounds, dialkali salt of 1,2-dicyano-1,2-dimercaptethene is reacted with 1,2-dihalogenoalkane, without difficulty, and indeed in accordance with the following formula:

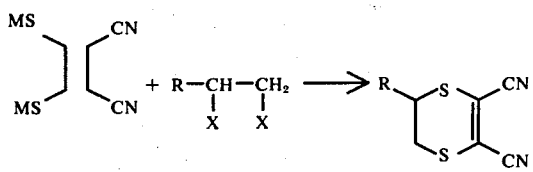

wherein
M stands for an alkali metal;
X stands for a halogene atom.

The preparation can be carried out, as a representative example, in the following way:

DETAILED DESCRIPTION OF THE INVENTION

Preparation of 5-propyl-2,3-dicyano-5,6-dihydro-p-dithiin (Compound IV)

9.3 g (0.05 mole) of di-sodium salt of 1,2-dicyano-1,2-dimercaptethene and 40 ml of dimethyl formamide (D.M.F.) were introduced in a reaction flask, of 100 ml, fitted with agitator, and then, 20 ml of D.M.F.-solution including 11.5 g (0.05 mole) of 1,2-dibromopentane were added dropwise at room temperature under agitation to the reaction mixture for 30 minutes.

Upon finishing the dropwise addition of said D.M.F.-solution, the reaction mixture was agitated for a further 2 hours, and the liquid state reaction mixture was treated in a reducing evaporator, so as to reduce its volume to about one fifth and the condensed liquid mixture was added to 200 ml of water, thereby precipitating yellow brown solids. These solids were filtered off, washed with water, and recrystallized from methanol to 7.3 g of white yellow crystals, m.p. :70° – 71° C. Yield: 69.5%.

In the similar way, other compounds I–III, V–VIII can be easily prepared.

These representative compounds I – VIII are listed in the following Table 1.

The infra red absorption curves of these compounds I – VIII are shown on the accompanying drawings.

Table 1

| Compound No. | Formula | Shape | m.p. (° C) |
|---|---|---|---|
| I | NC, S / NC, S (ring) | Colorless crystals | 134 – 5 |
| II | NC, S, CH₃ / NC, S | colorless crystals | 86 – 7 |
| III | NC, S, C₂H₅ / NC, S | colorless crystals | 34 – 5 |
| IV | NC, S, (CH₂)₂—CH₃ / NC, S | white yellow crystals | 70 – 1 |
| V | NC, S, CH(CH₃)₂ / NC, S | colorless needles | 86 – 7 |

Table 1-continued

| Compound No. | Formula | Shape | m.p. (° C) |
|---|---|---|---|
| VI | NC-C(=C(S-)S-)-CH$_2$-(CH$_2$)$_3$-CH$_3$ (cyclic dithio) with NC groups | white yellow oil | — |
| VII | NC-C(=C(S-)S-)-CH$_2$-(CH$_2$)$_4$-CH$_3$ (cyclic dithio) with NC groups | white yellow oil | — |
| VIII | NC-C(=C(S-)S-)-CH$_2$-(CH$_2$)$_5$-CH$_3$ (cyclic dithio) with NC groups | colorless crystals | 44 – 6 |

These compounds may be used per se, or preferably in the form of powdery composition, emulsion, suspension or solution, as the case may be, by addition of conventionally known carrier or diluent.

In the practical use of the fungicidal composition according to this invention, if necessary, a known extender, emulsifier, surfactant, wetting agent and/or the like auxiliaries may be added. Other kinds of fungicides, proper bacteriocides, insecticides and/or fertilizers may be combined in use, without deterioration of the fungicide according to this invention and with no fear of decomposition of such additives.

In the following, several representative fungicidal compositions according to this invention will be raised. However, it should be noted that the invention should not be limited only to these specifically selected embodiments. Kinds and ratios of the carriers, diluents, additives and auxiliaries may be varied in a broad range. Given parts are by weight, if not otherwise specified.

EXAMPLE 1 — POWDERY COMPOSITION

| compound No. II | 5 parts; |
|---|---|
| clay | 40 parts; |
| talc | 57 parts |

These materials are mixed together evenly and pulverized into a powdery composition ready for use.

EXAMPLE 2 — AQUEOUS COMPOSITION

|  | parts |
|---|---|
| compound No. VI | 50 |
| polyoxyethylene alkylaryl ether | 6 |
| kieselguhr | 44 |

These materials are mixed well with each other and added with water to provide a ready-for-use aqueous composition.

In the following, several experimental results will be given for the demonstration of superior fungicidal effects of the above mentioned compounds:

Experiment 1: Control of Powdery Mildew of Cucumber (*cucumis sativus*)

A number of flowerpots, each being of 10 cm-diameter, were used to culture cucumber plants, "Sagami-Hanjiro", a Japanese cucumber variety, one cucumber per one pot. Then, the plants were treated with aqueous suspensions of the hydrated composition mentioned in the foregoing Example 2 at different concentrations as per the numerical data to be given in the following Table 2. As the reference agent, called "control A", 6-methyl quinoxaline-2, 3-dithio carbonate was used in the similar way. All the cucumber leaves thus conditioned and dried, were inoculated in a green house with spores of *Sphaerotheca fuliginea* Pollacci by means of a hair pencil. After seven days following the inoculation, the affected leaves were visually inspected and classified in accordance with the following grades.

| grade | degree of affection |
|---|---|
| 0 | unaffected |
| 0.5 | less than 10% area of inoculated leaves affected |
| 1 | 10–20% area of inoculated leaves affected |
| 2 | 20–40% area of inoculated leaves affected |
| 3 | 40–60% area of inoculated leaves affected |
| 4 | 60–80% area of inoculated leaves affected |
| 5 | more than 80% area of inoculated leaves affected |

Table 2

| Compound No. | Concentration ppm | mean degree of affection | harmful effect of application of the chemical |
|---|---|---|---|
| I | 500 | 0 | None |
| II | 500 | 0 | " |
| III | 500 | 0.5 | " |
| IV | 500 | 0 | " |
| V | 500 | 0 | " |
| VI | 500 | 0 | " |
| VII | 500 | 0 | " |
| control A | 62.5 | 0 | " |
| non-conditioned | — | 5 | — |

Experiment 2: Control of Downy Mildew of Cucumber (*cucumis sativus*)

A number of flowerpots, each being of 10 cm-diameter, were used as before to culture cucumber plants, "Sagami-Hanjiro", a Japanese cucumber variety, one cucumber per one pot. Then, the plants were treated with aqueous suspensions of the hydrated composition mentioned in the foregoing Example 2 at different concentrations as per the numerical data to be given in the following Table 3. As the reference agent, called "control B", tetrachloroisophthalonitrile was used in the similar way. All the cucumber leaves thus conditioned and dried, were inoculated in a green house with spores of *Pseudoperonospora cubensis* Rostowzew by means of a hair pencil and kept at 22°–23° C in a highly humid atmosphere for 24 hours. After five days following the inoculation, the affected leaves were visually inspected and classified in the same way as adopted in the foregoing Experiment 1. The results are given in the following Table 3.

Table 3

| Compound No. | Concentration ppm | mean degree of affection | harmful effect of application of the chemical |
| --- | --- | --- | --- |
| I | 500 | 0 | None |
| II | " | 0 | " |
| III | " | 0.5 | " |
| IV | " | 0 | " |
| V | " | 0.5 | " |
| VI | " | 0.5 | " |
| VII | " | 0.5 | " |
| VIII | " | 0 | " |
| control B | 750 | 0 | " |
| non-conditioned | — | 5 | — |

Experiment 3: Control of rice blast.

A number of flowerpots were used to cultivate water rice plants, "Sasanishiki", a Japanese variety, in one-to-one relationship, and these plants were conditioned with an aqueous suspension of the hydrated compound set forth in the foregoing Example 2 at various concentrations given in the following Table 4, to such a degree that all the leaves of the plants were well wetted. Then, after being dried, the rice leaves were inoculated with an aqueous suspension of spores of *Pyricularia oryzae* Cavara by means of a spray gun and kept at 27°–28° C in a highly humid atmosphere in a green house.

Upon the lapse of four days after said inoculation, all the leaves were inspected visually for finding out the affected spots on the leaves. The control power, %, was calculated from the following formula:

$$= \left(1 - \frac{\text{number of affected spots found on leaves conditioned}}{\text{similar number of affected spots on the corresponding number of flower pots, non-conditioned}}\right) \times 100$$

The results are given in the following Table 4. As the reference compound, O, O-diisopropyl-S-benzyl thiophosphate, which is called "control C" in the same Table.

Table 4

| Compound No. | Concentration, ppm | number of affected spots | control power, % | harmful effect of application of the chemical |
| --- | --- | --- | --- | --- |
| I | 500 | 21 | 97.5 | None |
|  |  | (58) | (92.4) | (") |
| II | " | 12 | 98.6 | " |
|  |  | (112) | (85.4) | (") |
| III | " | 129 | 84.6 | " |
| IV | " | 11 | 98.7 | " |
| V | " | 23 | 97.2 | " |
| VI | " | 9 | 98.9 | " |
| VII | " | 8 | 99.0 | " |
| VIII | " | 15 | 98.2 | " |
| Control C | 480 | 24 | 97.1 | " |
|  | (480) | (130) | (83.0) | (") |
| non-conditioned | — | 83.6 | — | — |
|  | (—) | (76.5) |  | (—) |

Remarks: parenthesized numerals, were obtained with another similar experiment carried out at a different season.

Experiment 4: control of Helminthosporium Rice Leaf Spots

Rice plants were cultured and controlled in the similar way as adopted in the foregoing Experiment 3. The inoculation was carried out with spores of *Cochliobolus miyabeanus* Drechsler. As the reference, 2,4-dichloro-6-(o-chloroanilino) 1,3,5-triazine, called "control D" was adopted. The control power was calculated by the foregoing formula adopted in Experiment 3. The inoculation was carried out by spraying and the inoculated plants were held at 27° – 28° C in a highly humid atmosphere. The visual inspection of the affected spots was made after four days following inoculation.

The results are given in the following Table 5.

Table 5

| Compound No. | Concentration, ppm | number of affected spots | control power, % | harmful effect of application of the chemical |
| --- | --- | --- | --- | --- |
| I | 500 | 158 | 87.5 | None |
| II | 500 | 132 | 89.6 | " |
| Control D | 625 | 171 | 86.5 | " |
| non-conditioned | — | 1,264 | — | — |

The embodiments of the invention in which an exclusive property or privilege is claimed are as follows:

1. A method for the treatment of fungus diseases in plants comprising applying to fungi a fungicidally effective amount of a composition comprising an inert carrier and an active ingredient having the formula:

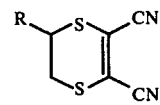

wherein R is H, isopropyl, or n-alkyl having 1 to 6 carbon atoms.

2. The method of claim 1, wherein R is H.

3. The method of claim 1, wherein R has the formula

—CH$_2$—CH$_3$.

4. The method of claim 1, wherein R has the formula

—(CH$_2$)$_2$—CH$_3$.

5. The method of claim 1, wherein R has the formula

6. The method of claim 1, wherein R has the formula —(CH$_2$)$_3$—CH$_3$.

7. The method of claim 1, wherein R has the formula —(CH$_2$)$_4$—CH$_3$.

8. The method of claim 1, wherein R has the formula —(CH$_2$)$_5$—CH$_3$.

* * * * *